United States Patent [19]  
Imada et al.

[11] Patent Number: 4,518,529  
[45] Date of Patent: May 21, 1985

[54] ANTIBIOTICS C-19393S$_2$

[75] Inventors: Akira Imada, Nishinomiya; Setsuo Harada, Kawanishi; Mitsuko Asai, Takatsuki, all of Japan

[73] Assignee: Takeda Chemical Industries, Ltd., Osaka, Japan

[21] Appl. No.: 113,132

[22] Filed: Jan. 17, 1980

[30] Foreign Application Priority Data

Feb. 2, 1979 [JP] Japan .................................. 54-11560
Jun. 26, 1979 [JP] Japan .................................. 54-81141

[51] Int. Cl.$^3$ .................... C07D 487/04; A61K 31/40
[52] U.S. Cl. ............................................. 260/245.2 T
[58] Field of Search .................. 260/245.2 T; 424/274

[56] References Cited

U.S. PATENT DOCUMENTS 4,172,129 10/1979 Cole et al. .................... 260/245.2 T
4,210,662 7/1980 Eglington ..................... 260/245.2 T
4,211,707 7/1980 Ratcliffe ...................... 260/245.2 T
4,223,038 9/1980 Small ........................... 260/245.2 T
4,232,036 11/1980 Christenson .................. 260/245.2 T

FOREIGN PATENT DOCUMENTS 2047700 12/1980 United Kingdom .

OTHER PUBLICATIONS

Maeda, et al., J. Antibiotics 30, 770–772, (1977).
Oilonogi et al., J. Antibiotics 34, 212–217, (1981).

Primary Examiner—Nicholas S. Rizzo  
Attorney, Agent, or Firm—Wenderoth, Lind & Ponack

[57] ABSTRACT

Novel antibiotics C-19393S$_2$ and H$_2$, which are produced by cultivating a microorganism belonging to the genus Streptomyces, are useful as a bactericide or disinfectant, and particularly, Antibiotic C-19393S$_2$ produces a synergistic effect with penicillin and/or cephalosporin antibiotic agents.

1 Claim, 4 Drawing Figures

ANTIBIOTICS C-19393S₂

This invention relates to Antibiotics C-19393S₂ and H₂ which are novel antibiotics, respectively, and the salts thereof, and to a method for producing Antibiotics C-19393S₂ and/or H₂.

The present inventors isolated a number of microorganisms from soil samples and investigated the antibiotics produced by the microorganisms for the purpose of exploration and investigation of novel antibiotics. As the result of such investigations, it was found that a certain microorganism is capable of producing novel antibiotics that this microorganism belongs to the genus Streptomyces, that cultivation of this microorganism in a suitable culture medium results in an accumulation of the antibiotics in the culture broth and that said antibiotics have antimicrobial activity against gram-positive and gram-negative bacteria. The present inventors isolated the above antibiotics which were confirmed to be novel antibiotics from their chemical and physical properties and to have the following formula (I):

(wherein R is —SO₃H or hydrogen).

In the formula (I), the compound in which R is —SO₃H was designated as Antibiotic C-19393S₂ and the compound in which R is hydrogen was designated as Antibiotic C-19393H₂.

This invention is therefore directed to:

(1) Antibiotic C-19393 S₂ or H₂ which are represented by the formula:

(wherein R is —SO₃H or hydrogen); and (2) A method for producing Antibiotics C-19393S₂ and/or H₂ characterized in that said method comprises cultivating a microorganism which belongs to the genus Streptomyces and is capable of producing Antibiotics C-19393S₂ and/or H₂ in a culture medium to cause the microorganism to elaborate and accumulate Antibiotics C-19393S₂ and/or H₂ in the culture broth, and recovering the Antibiotics C-19393S₂ and/or H₂ from said broth.

In the context of this invention, Antibiotic C-19393S₂ is hereinafter sometimes referred to briefly as "C-19393S₂", and Antibiotic C-19393H₂ is hereinafter sometimes referred to briefly as "C-19393H₂".

To produce Antibiotics C-19393S₂ and/or H₂ of the present invention, Antibiotics C-19393S₂ and/or H₂-producing microorganism belonging to the genus Streptomyces is employed. A typical example of the microorganism is Streptomyces sp. strain C-19393 (hereinafter sometimes referred to as "C-19393 strain") which is obtained by plating a suspension of a soil sample, collected in Sweden, in sterile water onto a culture medium composed of 1% soluble starch, 0.05% urea, 0.05% Polypepton (Daigo Nutritive Chemicals, Ltd., Japan), 0.05% yeast extract (Difco, United States), 0.02% dipotassium phosphate, 0.02% potassium chloride, 0.01% magnesium sulfate, 5 µg/ml of bleomycin and 2% agar having a pH of 7.0, and repeatedly purifying the micoorganism from the colony formed upon cultivation at 28° C. for 2 weeks.

The microbiological characteristics of Streptomyces sp. strain C-19393 are as follows:

(a) Morphological Characteristics:

The aerial mycelium having a width of about 1µ extends from the well-branched vegetative mycelium and is monopodially branched from the main axis to form side chains. Straight or slightly flexous spore chains, i.e., so-called "rectus flexibilis" (hereinafter abbreviated as "RF") are observed at the end of the side chain. Each spore is cylindrical in shape (0.35–0.55µ×0.7–1.4µ) and has a smooth surface. Neither specific organs such as spherical sporangia and sclerotia nor motile spores are observed.

(b) Cultural Characteristics:

The cultural characteristics of the strain on various media are shown below in Table 1. Unless otherwise indicated, the characteristics were observed after cultivation at 28° C. for 2 weeks.

TABLE 1

| Medium | Growth | Aerial Mycelium | Reverse | Soluble Pigment |
|---|---|---|---|---|
| Sucrose nitrate agar | Moderate | White | Colorless | None |
| Glucose asparagine agar | Slight | White | Colorless | None |
| Glycerin asparagine agar | Moderate | White | Colorless | None |
| Starch agar | Moderate | None | Ocher | None |
| Nutrient agar | Moderate | White | Ivory | None |
| Tyrosine agar | Moderate | None | Colorless | None |
| Yeast extract malt extract agar | Moderate | None | Grayish yellow | None |
| Oatmeal agar | Moderate | White | Colorless | None |

C-19393 strain shows luxuriant growth on a medium comprising 2% oatmeal, 2% tomato paste, 0.2% bovril (manufactured by Bovril, England) and 2% agar and having a pH 7.0 (hereinafter referred to as "T Medium") and grayish yellow aerial mycelia are abundantly formed. No soluble pigment is produced.

(c) Physiological characteristics:

(1) Temperature range for growth:
lower limit: lower than 15° C.
upper limit: 32° to 35° C.
optimum temperature: 26.5° to 30° C.

(2) Liquefaction of gelatin: Positive.

(3) Hydrolysis of starch: Positive.

(4) Peptonization of skimmed milk: Positive.
Coagulation of skimmed milk: Negative.

(5) Production of melanoid pigments:
tyrosin-agar: Negative
peptone-yeast extract-iron-agar: Negative (6) Assimilation of carbon sources (Pridham-Gottlieb agar) is shown below in Table 2.

TABLE 2

| Carbon Sources | Assimilation |
|---|---|
| Glycerin | + |

TABLE 2-continued

| Carbon Sources | Assimilation |
| --- | --- |
| i-Inositol | ± |
| D-Mannitol | − |
| D-Xylose | + |
| L-Arabinose | + |
| D-Glucose | + |
| D-Galactose | + |
| D-Fructose | + |
| Maltose | + |
| Sucrose | − |
| Rhamnose | + |
| Raffinose | − |
| Starch | + |
| Cellulose | ± |
| Control (No addition) | − |

Note:
−: No growth
±: Doubtful growth
+: Growth

From the above various characteristics, the C-19393 strain apparently belongs to the genus Streptomyces. The present inventors investigated the taxonomical position of the C-19393 strain based on the above observations that the strain develops white to yellow aerial mycelium, the spore chain is RF, the spore surface is smooth, melanoid pigments and soluble pigments are not produced on media, no definite reverse color is observed and the strain does not utilize mannitol, with reference to the following literature:

Reference 1: S. A. Waksman, "The Actinomycetes", Vol. 2, 1961.

Reference 2. Bergey's Manual of Determinative Bacteriology, 8th Edition, 1974.

Reference 3. E. B. Shirling and D. Gottlieb, "International Journal of Systematic Bacteriology", Vol. 18, pp 69–189, 1968; ibid, Vol. 18, pp 279–392, 1968; ibid, Vol. 19, pp 391–512, 1969; and ibid, Vol. 22, pp 265–394, 1972.

However, the present inventors did not find any strain which shared all of the above characteristics of C-19393 strain in References 1 to 3. Thus, the present inventors compared the strain with 7 strains described in Reference 2, at page 751, Table 17.41b which are characterized by white aerial mycelia, RF, negative melanoid pigment production and smooth spore surface, but *Streptomyces galtieri*, which does not utilize mannitol, differs from C-19393 strain in that the former does not grow on a sucrose-nitrate medium (hereinafter referred to as "Czapek") and, besides, kinds of sources to be utilized by the C-19393 strain and *S. galtieri* are often different. Of the strains shown in Table 17.41b, *Streptomyces albovinaceus* is similar to C-19393 strain in the utilization of carbon sources other than mannitol, but is different from C-19393 strain in that the former produces red to pink soluble pigments.

Of 41 strains listed in Table 17.43b at pages 795–796 in Reference 2 which are characterized by yellow aerial mycelium, RF, negative melanoid pigment production and smooth spore surface, only *Streptomyces canescens* does not utilize mannitol but this strain differs from C-19393 strain in that the former grows only slightly on Czapek and, in addition, does not utilize xylose and rhamnose. Strains similar to C-19393 strain in the utilization of carbon sources other than mannitol are described below, but each of these strains differs from C-19393 strain in the items shown in the parentheses. Th color of aerial mycelium and production of soluble pigments were directly compared among C-19393 strain and the typical strains of respective species. *Streptomyces chrysomallus* (color of aerial mycelium and production of soluble pigments), *Streptomyces citreofluorescens* (color of aerial mycelium and production of soluble pigments), *Streptomyces fimicarius* (poor growth on Czapek), *Streptomyces globisporus* (large spore diameter, weak starch utilization), *Streptomyces globisporus* subsp. *vulgaris* (poor growth on Czapek), *Streptomyces griseinus* (poor growth on Czapek and coagulation of skim milk), *Streptomyces parvus* (production of soluble pigments and large spore diameter), and *Streptomyces setonii* (poor growth on Czapek and production of soluble pigments).

Further, of the International Streptomyces Project (ISP) strains described in Reference 3, a total of 34 strains which are characterized by having white to yellow aerial mycelium, producing no melanoid pigment, having no definite reverse color, producing no soluble pigment and having RF spore chains and smooth spore surface were directly compared and investigated with reference to References 1, 2 and 3 and, if necessary, to the originals of these references, by cultivating the strain on "T Medium" on which C-19393 strain exhibits relatively characteristic cultural properties and it was found that *Streptomyces saprophyticus* exhibits properties relatively similar to those of C-19393 strain. However, C-19393 strain has a distinct characteristic feature in that is is not capable of assimilating mannitol which is assimilable by most of the species belonging to the genus Streptomyces having white to yellow aerial mycelium and, therefore, is clearly different from the above-mentioned *Streptomyces saprophyticus*. Accordingly, the present inventors identified C-19393 strain as a novel species and designated it as Streptomyces sp. C-19393. This strain has been deposited at Fermentation Research Institute, Agency of Industrial Science and Technology, Tsukuba, Japan, with the accession number of FERM-P No. 4774; Institute for Fermentation, Osaka, Japan, with the accession number of IFO 13886; the American Type Culture Collection, United States, with the accession number of ATCC 31486; and with the U.S. Department of Agriculture, Northern Regional Research Center, Peoria, Ill., United States, with the accession number NRRL 15037.

While C-19393 strain has been described above, it is well known that various properties of Streptomyces are not definite and are very liable to spontaneously or artificially undergo mutation. Thus, the strain which can be used in the present invention includes any strain which belongs to the genus Streptomyces and is capable of producing Antibiotics C-19393$S_2$ and/or $H_2$.

The cultivation according to the method for producing the antibiotic of the present invention can be conducted by growing the above strain in a culture medium containing nutrients which are assimilable to microorganisms. The carbon sources as a medium component can, for example, be glucose, starch, glycerin, dextrin, sucrose, millet jelly, molasses, etc. Examples of nitrogen sources are meat extract, dried yeast, yeast extract, soybean meal, corn steep liquor, wheat embryo bud, cottonseed flour, ammonium sulfate, ammonium nitrate, etc. If necessary, inorganic salts such as calcium carbonate, sodium chloride, potassium chloride, a phosphoric acid salt, etc. as well as organic and inorganic substances which assist in growth of the microorganism and promote the production of Antibiotics C-19393$S_2$ and $H_2$ can be added to the medium in appropriate amounts.

Also, salts of heavy metals such as ferrous sulfate, copper sulfate, etc. and vitamins such as vitamin $B_1$, biotin, etc. may be added to the medium, if necessary. Further, antifoams and surfactants such as silicone oil, polyalkylene glycol ether, etc. may be added to the medium. Other organic and inorganic substances which aid the growth of microorganism and promote the production of $C-19393S_2$ and/or $H_2$ can be added to the medium in suitable amounts.

The cultivation can be carried out by the conventional procedure which is generally used for the production of antibiotics and may be either solid-medium cultivation or liquid-medium cultivation. The liquid-medium cultivation may be achieved by stationary culture, agitated culture, shake culture or aerobic culture, but is preferably conducted by agitated culture under aeration. The cultivation is preferably conducted at a temperature of about 15° C. to about 32° C. at a pH of about 4 to about 8 for a period of about 8 hours to about 168 hours, preferably 24 to 144 hours.

The antibiotics $C-19393S_2$ and $H_2$ are predominantly produced extra-cellularly in the fermentation broth and therefore it is advantageous to separate the resulting culture into microbial cells and a supernatant fluid by centrifugation or filtration and then to isolate the desired antibiotic from the supernatant fluid. However, the desired antibiotic can also be obtained directly from the fermentation broth.

Assay of the potency of the product thus obtained may be performed against *Comamonas terrigena* IFO 13299 as the test organism and using $C-19393S_2$ or $H_2$ as the standard by the cylinder-plate method or paper disc method employing a bouillon agar medium or TSA [Trypticase Soy Agar (Baltimore Biological Laboratory, United States)].

The isolation of $C-19393S_2$ and $H_2$ can be carried out by the procedure generally used for isolation of metabolites produced by microorganisms. For example, since $C-19393S_2$ and $H_2$ are water-soluble acidic substances produced for the most part extracellularly, a procedure comprising removing the microbial cells by filtration or centrifugation and separating, purifying and harvesting the active substance from the filtrate is generally used for isolating $C-19393S_2$ and $H_2$. That is, various means by taking advantage of difference in solubility bahavior and degree in various solvents, difference in precipitation behavior or rate, the difference in adsorption affinity, as well as ion-exchange chromatography, molecular-sieve chromatography, concentration under reduced pressure and freeze-drying, etc. can be used alone or in a suitable combination, in any order or in repetition. Examples of adsorbents which can be used are activated carbon, adsorptive resins, anion-exchange resins, powdered cellulose, silica gel, etc., or carriers having a molecular sieve properties. Examples of eluting solvents which can be used are aqueous solutions of water-soluble organic solvents such as acetone, methanol, ethanol, propanol, butanol, isopropanol, isobutanol and the like, or aqueous solutions or acids or alkalis, or a buffer, or aqueous solutions of inorganic or organic salts, though the solvents which can be useful differ depending upon the type of carrier.

As to $C-19393S_2$, more specifically, the fermentation broth obtained after completion of cultivation is filtered using a filter aid to remove microbial cells. The resulting filtrate is passed through a column of activated carbon under neutral or weakly acidic conditions and the adsorbed $C-19393S_2$ is eluted with a hydrophilic solvent system. Most of antibacterial activity is found in the aqueous eluate. Since the antibiotic substance of the present invention is acidic in nature, anionic exchange resins of $Cl^-$ or $CH_3COO^-$ type such as Amberlite IRA-400, 402 and 410 (Rohm & Haas Co., United States), Dowex-1 (Dow and Chemical Co., United States), Diaion SA-21A and C (Mitsubishi Chemical Industries, Japan) can be used advantageously for further purification. The antibiotic substance is further eluted with an aqueous sodium chloride solution or a buffer solution. The desalting of the eluate can be achieved by rendering the eluate weakly acidic and subjecting again the eluate to activated carbon chromatography, followed by elution with aqueous alcohol, etc. The eluate containing the active substance is concentrated under reduced pressure at a low temperature and methanol or ethanol is added to the concentrate. The precipitate formed is removed by filtration and the resulting aqueous alcohol solution is again concentrated under reduced pressure. To the concentrated residue is added acetone or the like and the precipitate is separated by filtration. The powder thus obtained can be further purified advantageously by column chromatography using a combination of DEAE or QAE Sephadex in $Cl^-$ form (Pharmacia Co., Sweden) and an adsorbent resin XAD (Rohm and Haas Co., United States) or Diaion High Porous Type Resin HP-20 (Mitsubishi Chemical Industries, Japan, hereinafter sometimes referred to as "Diaion HP-20"). That is, an aqueous solution of the powder obtained above is passed through and adsorbed on DEAE Sephadex A-25 ($Cl^-$ form) and, after washing with water, the column is eluted with 0.4M aqueous sodium chloride. The eluate is adjusted to pH 5 and subjected to activated carbon column chromatography. The elution from the activated carbon column is carried out using aqueous isobutanol, but a better result can be obtained by elution under neutral or weakly basic conditions adjusted by addition of dilute aqueous ammonia or the like. The resulting substance is then subjected to column chromatography using XAD-II or Diaion HP-20. The active substance adsorbed is fractionally eluted with water. The active fractions are collected and concentrated, and the concentrate is subjected to column chromatography using QAE-Sephadex A-25 ($Cl^-$ form), followed by elution with 0.2M aqueous sodium chloride. The eluate is desalted by activated carbon chromatography in the same manner as described above. The eluate is concentrated and the concentrate is subjected to XAD-II column chromatography, followed by elution and fractionation with water. These fractions are found to include fractions showing a single peak on a liquid chromatogram as described hereinafter. The active fractions are pooled and concentrated to dryness under reduced pressure at a low temperature, and acetone, or the like is added to the residue to obtain $C-19393S_2$.

As to Antibiotic $H_2$, more specifically, the fermentation broth obtained after completion of cultivation is filtered using a filter aid to remove microbial cells. The resulting filtrate is passed through a column of activated carbon under neutral or weakly acidic conditions and the adsorbed $C-19393H_2$ is eluted with a hydrophilic solvent system. Since the antibiotic substance of the present invention is acidic in nature, anionic exchange resins of $Cl^-$ or $CH_3COO^-$ form such as Amberlite IRA-400, 402, 410, Dowex-1, Diaion SA-21A and C can be used advantageously for further purification. An active substance is further eluted with an aqueous sodium chloride solution or a buffer solution. The de-salting of the eluate can be achieved by rendering the eluate neutral or weakly acidic and subjecting again the eluate to activated carbon chromatography, followed by elution with aqueous alcohol, etc. The eluate containing the active substance is concentrated under reduced pressure at a low temperature and methanol or ethanol is added to the concentrate. The precipitate formed is removed by filtration and the resulting aqueous alcohol solution is again concentrated under reduced pressure. For further purification of the resulting concentrate, column chromatography using a combination of DEAE or QAE Sephadex in Cl$^-$ form and an adsorbent resin XAD or Diaion HP-20 can be used advantageously. That is, the concentrate obtained previously is passed through Diaion HP-20 and fractionally eluted with water. The active fractions are concentrated and the concentrate is passed through DEAE Sephadex A-25 (Cl$^-$ form). After washing with 0.02M aqueous sodium chloride, elution is carried out with 0.05M aqueous sodium chloride. The resulting eluate is then passed through Diaion HP-20 which has been treated with an aqueous sodium chloride solution and elution is carried out with an aqueous sodium chloride solution containing methanol. The desalting of the eluate is carried out using activated carbon chromatography in the same manner as described above. The resulting eluate is concentrated and the concentrate is subjected to column chromatography using Diaion HP-20 (50 to 100 mesh) and fractionally eluted with water. The active fractions are pooled and concentrated, and the concentrate is subjected to column chromatography using QAE Sephadex A-25 (Cl$^-$ form) which has been treated with 0.02M aqueous sodium chloride. The fractionation is carried out using 0.04M aqueous sodium chloride and the active fractions are de-salted in the same manner as described above using activated carbon chromatography. The eluate is concentrated and the concentrate is subjected to column chromatography using Avicel (crystalline cellulose) (manufactured by Asahi Chemical Industry Co., Ltd., Japan) and the column is eluted and fractionated with 90% aqueous propanol. The eluate is concentrated and the concentrate is subjected to column chromatography using XAD-II (100 to 200 mesh), followed by elution and fractionation with water. The active fractions are concentrated and the concentrate is subjected to a preparative liquid chromatography, followed by elution and fractionation with a methanol-containing phosphate buffer. Fractions showing a single peak are pooled and concentrated, and the concentrate is subjected to column chromatography using Diaion HP-20 (100 to 200 mesh), followed by elution with water to remove the buffer. The eluted active fractions are concentrated under reduced pressure at a low temperature and the concentrate is freeze-dried to obtain C-19393H$_2$ as white powder.

The present compounds can form respectively, alkali metal salts or an ammonium salts. Examples of metal salts of each component are the sodium salt, potassium salt, lithium salt, etc.

The physical and chemical properties of C-19393S$_2$ disodium salt, as obtained in Example 1 hereinafter described, are as follows:

(1) Appearance: White powder.

(2) Specific rotation: $[\alpha]_D^{22} - 152° \pm 15°$ (c=0.5, in water).

(3) Elemental Analysis (%): (Sample dried over phosphorus pentoxide at 40° C. for 6 hours): C, 36.28±1.0, H, 3.72±0.5, N, 6.07±0.5, Na, 9.70±1.0, O, 31.09*, S, 13.13±1.0, *(The oxygen content is a balance calculated by subtracting the contents of others).

(4) Molecular weight (calculated as containing two Na atoms per molecule) 528–429.

(5) Molecular formula:
Estimated molecular formula: $C_{14}H_{16}N_2Na_2O_9S_2$.

Figure 1:
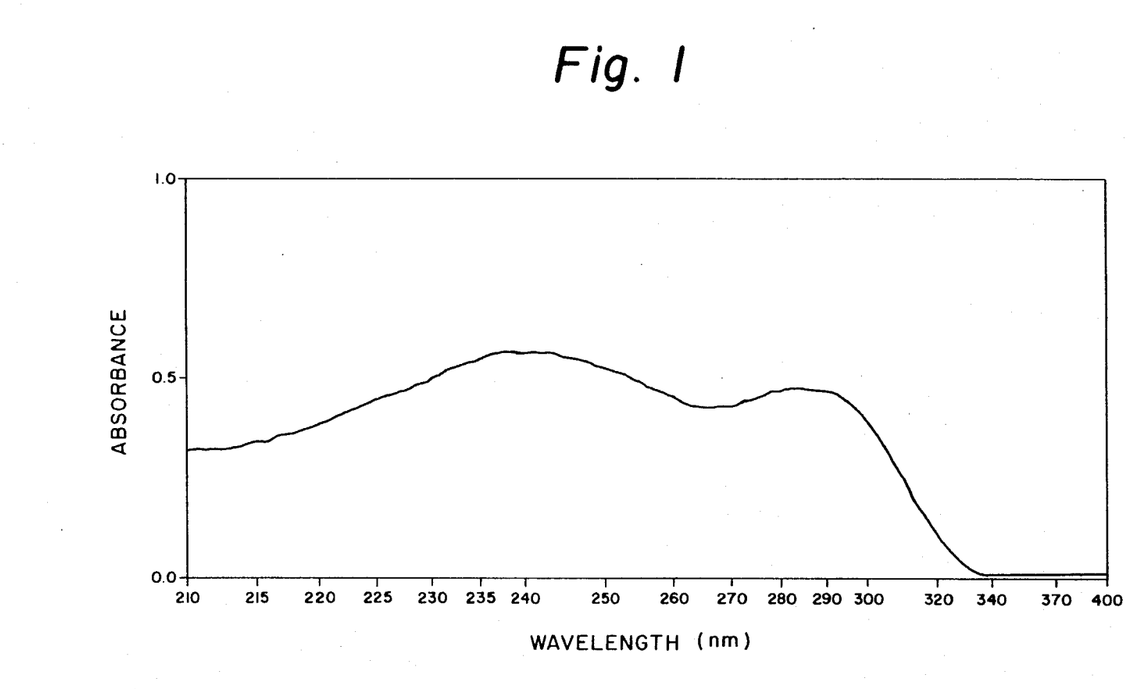

(6) Ultraviolet absorption spectrum:
The spectrum measured in water is shown in FIG. 1 and the maximum values are as follows: $\lambda_{max}^{H_2O}$: 240±2 nm ($E_1{}_{cm}{}^{1\%}=296\pm20$) and 285±2 nm, ($E_1{}_{cm}{}^{1\%}=245\pm20$).

Figure 2:
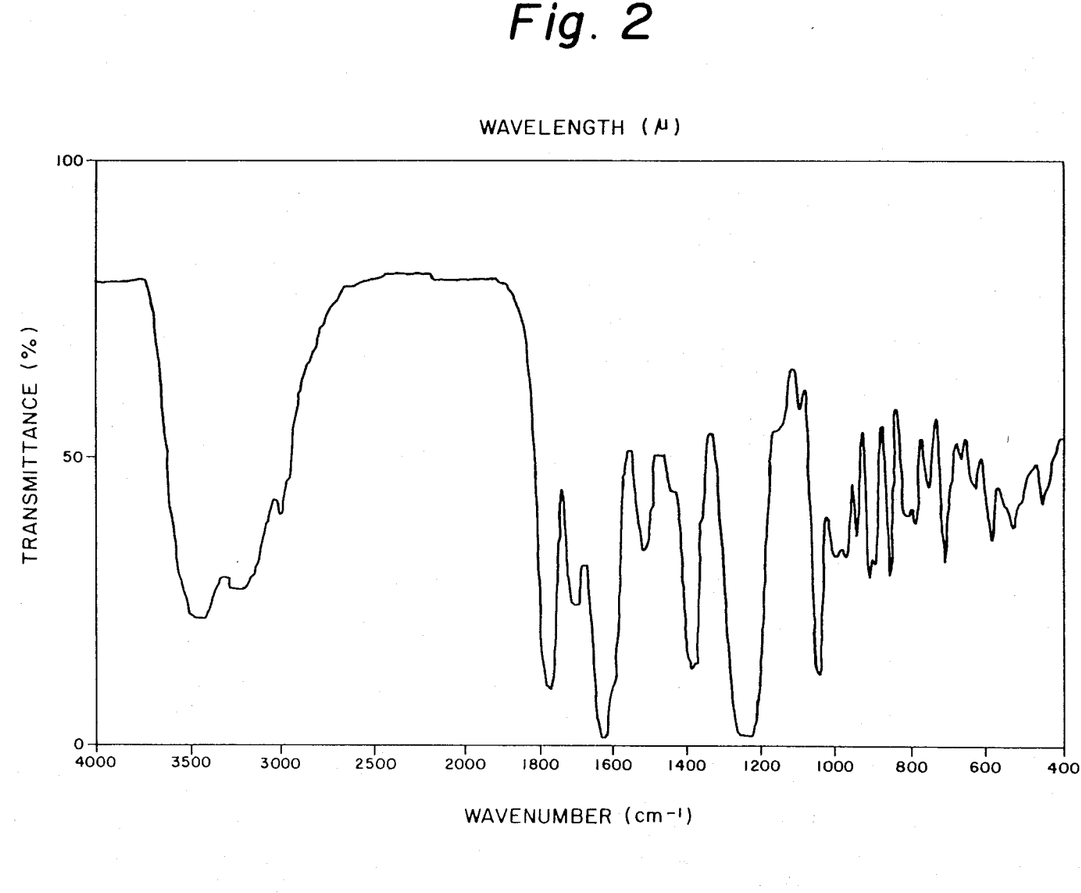

(7) Infrared absorption spectrum:
The spectrum measured as potassium bromide tablet is shown in FIG. 2 and principal peaks (wave numbers) are as follows: 3450, 3220, 3000, 1770, 1700, 1630, 1515, 1395, 1240–1260, 1100, 1050, 1010, 980, 950, 915, 900, 860, 815, 795, 760, 715, 670, 625, 590, 530(cm$^{-1}$).

(8) Thin-layer chromatography [Cellulose f (Tokyo Kasei Co., Ltd., Japan)].

| Solvent system | Rf value |
| --- | --- |
| (a) propanol:water (4:1) | 0.33 ± 0.1 |
| (b) butanol:acetic acid:water (2:2:1) | 0.54 ± 0.1 |
| (c) propanol:ethanol:water (5:2:3) | 0.62 ± 0.1 |

(9) High performance liquid chromatography (Waters Associates Inc., United States).

(a) Microbondapak C$_{18}$/5% methanol-0.02M citrate buffer (pH 6.3), 1.5 ml/min./cm (2400 psi); Rt=9.0(min.)±1 (min.).

(b) Microbondapak NH$_2$/70% methanol-0.02M borate buffer (pH 7.5), 1.5 ml/min./cm (2300 psi); Rt=7.0 (min.)±1(min.).

(10) Solubility:
Insoluble in chloroform, ethyl acetate, acetone; sparingly soluble in ethanol, butanol, pyridine; soluble in methanol, dimethyl sulfoxide, acetic acid; readily soluble in water (11) Color reactions:
Positive: Ehrlich and potassium permanganate reactions.

Negative: Ninhydrin, Greig-Leaback, Dragendorff, ferric chloride and Sakaguchi reactions.

The physical and chemical properties of C-19393H$_2$ sodium salt obtained in Example 2 hereinafter described are as follows:

(1) Appearance: white powder.

(2) Elemental analysis (%) (determined on the sample dried over phosphorus pentoxide at 40° C. for 6 hours): C, 45.34±1.0, H, 4.98±0.5, N, 7.48±0.5, Na, 6.15±1.0, S, 8.51±1.0.

(3) Molecular weight (calculated as containing one Na atom per molecule) 426–322.

(4) Molecular formula: Estimated molecular formula: $C_{14}H_{17}N_2NaSO_6$.

(5) Specific rotation: $[\alpha]_D^{26} - 134°$(c=0.156, in water).

Figure 3:
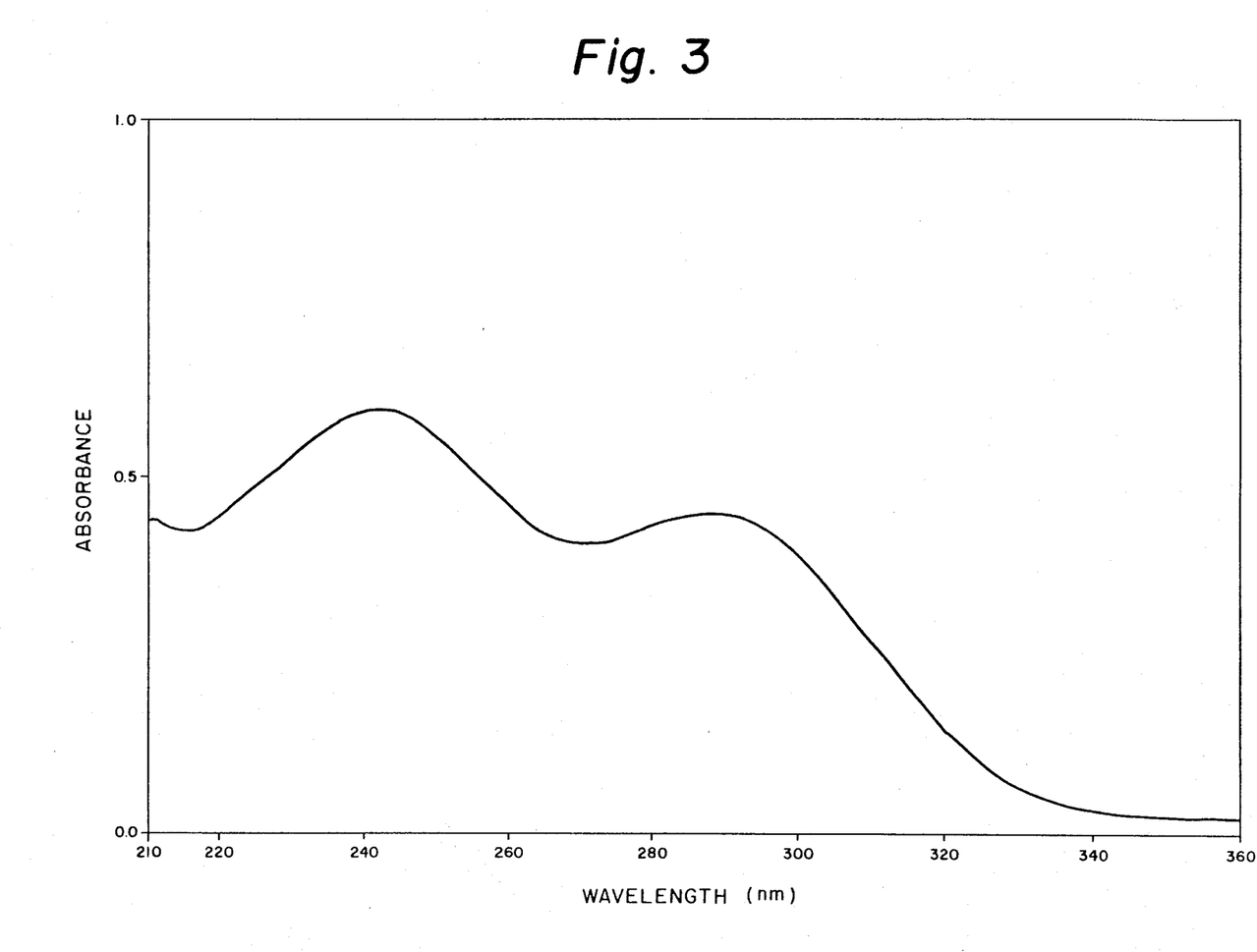

(6) Ultraviolet absorption spectrum:
The spectrum measured in water is shown in FIG. 3 and the maximum values are as follows: $\lambda_{max}^{H_2O}(E_1{}_{cm}{}^{1\%})=242\pm2$ nm (395±20) and 289±2 nm, (314±20).

Figure 4:
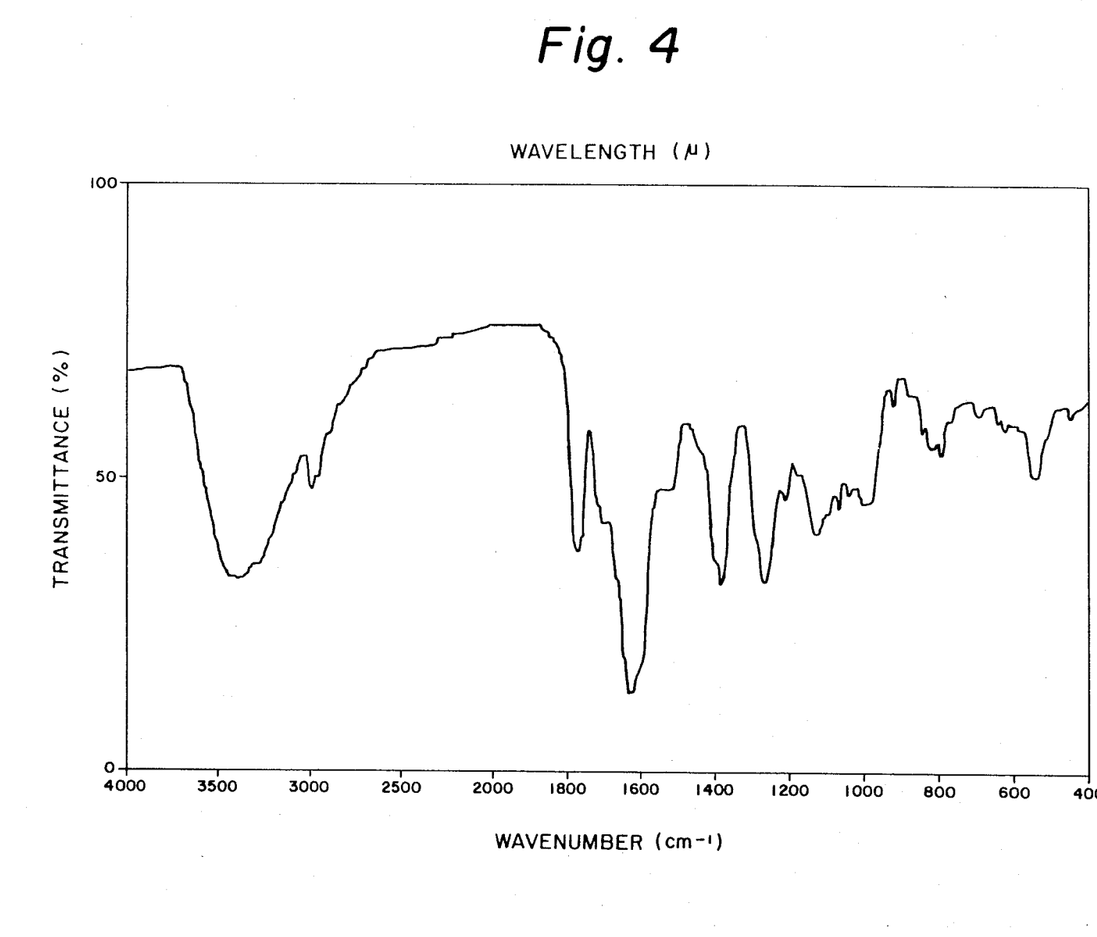

(7) Infrared absorption spectrum:
The spectrum measured as potassium bromide tablet is shown in FIG. 4 and principal peaks (wave number)

are as follows: 3400, 2980, 2940, 1770, 1700, 1630, 1530, 1390, 1265, 1215, 1130, 1090, 1065, 1040, 1000, 920, 840, 820, 790, 770, 700, 620, 540, 450(cm$^{-1}$).

(8) Circular dichroism spectrum (in water):

Positive Cotton effect at 234 nm, and negative Cotton effect at 206, 258 and 292 nm.

(9) Thin layer chromatography [using Cellulose f (Tokyo Kasei Co., Ltd., Japan)]:

| Solvent system | Rf value |
|---|---|
| (a) Propanol:water (4:1) | 0.45 ± 0.1 |
| (b) Butanol:acetic acid:water (2:1:1) | 0.67 ± 0.1 |
| (c) Butanol:pyridine:acetic acid:water (15:3:2:12), upper layer | 0.45 ± 0.1 |

(10) High performance liquid chromatography (Waters Co., Ltd., United States):

(a) Microbondapak $C_{18}$/8% methanol—0.02M phosphate buffer (pH, 6.3), 2.0 ml/min./cm (1900 psi); Rt=5.3±1.0 (min.).

(b) Microbondapak $NH_2$/5% methanol—0.02M phosphate buffer (pH 5.7), 1.3 ml/min./cm (3000 psi); Rt=4.8±1.0 (min.).

(11) Color reactions:

Positive: Ehrlich, potassium permanganate reactions.

Negative: Ninhydrin, Greig-Leaback, Dragendorff, ferric chloride and Sakaguchi reactions.

(12) Solubility: Insoluble in chloroform and ethyl acetate; sparingly soluble in acetone, ethanol and butanol; soluble in methanol and water.

From the various properties described above, Antibiotics C-19393S$_2$ and H$_2$ were estimated to be respectively β-lactam type antibiotics, and on the basis of each elemental analysis value and estimated molecular weight, the estimated molecular formulae: $C_{14}H_{16}N_2Na_2O_9S_2$ and $C_{14}H_{17}N_2NaO_6S$ were given to C-19393S$_2$ and H$_2$, respectively. Judging from the fact that both the antibiotics have the maximum values of $\lambda_{max}^{H2O}$ 241±3 nm and 287±4 nm on ultraviolet absorption spectrum, it was estimated that, the present antibiotics have the same chromophore as in MM-4550 among the known β-lactam type antibiotics.

Table 3 shows comparative data of $^1$H-NMR spectra of these three antibiotics namely:

In C-19393S$_2$, two CH$_3$ signals (δ1.66 ppm, 3H, s, 1.73 ppm, 3H,s) are observed in the region of CH$_3$ proton, unlike in MM-4550; in C-19393H$_2$, two CH$_3$ signals (δ1.36 ppm, 3H, s; 1.47 ppm, 3H,s) are also observed; H$_8$ proton (δ4.97 ppm, 1H, m) observed in MM-4550 is observed in neither C-19393S$_2$ nor H$_2$; chemical shifts of the remaining proton signals are substantially the same with one another coupling constants of H$_4$-H$_5$ and H$_5$-H$_6$ obtained by spin decoupling by means of H$_5$ irradiation are the same in value; in C-19393S$_2$, the presence of SO$_3^-$ is confirmed by the strong absorptions at $\nu_{max}^{KBr}$ 1260 and 1050 cm$^{-1}$ of IR spectrum; and, in C-19393H$_2$, the above-mentioned absorption due to SO$_3^-$ is not observed in IR spectrum.

Thus, the formula (I) was assigned to C-19393S$_2$ and C-19393H$_2$, respectively.

TABLE 3

$^1$H.NMR Spectra of C-19393 S$_2$ and H$_2$

| | | H$_2$ | S$_2$ | MM-4550[1] |
|---|---|---|---|---|
| (100 MHz, D$_2$O, TMS) (3 mg/0.4 ml) | 8-CH$_3$ | 1.36 (3H,s) | 1.66 (3H,s) | 1.45* (3H,d, J = 6.5 |
| | 8-CH$_3$ | 1.47 (3H,s) | 1.73 (3H,s) | |
| | N—Ac | 2.16 (3H,s) | 2.16 (3H,s) | 2.05 (3H,s) |
| | H$_{4a}$ | 3.08 (dd, J$_{4Ha,5H}$ = 9, J$_{4Ha,b}$ = 18) | 3.10 (dd, J$_{4Ha,5H}$ = 9, J$_{4Ha,b}$ = 18) | 2.99 (dd, J$_{4Ha,5H}$ = 9, J$_{4Ha,b}$ = 18.5) |
| | H$_{4b}$ | 3.93 (dd, J$_{4Hb,5H}$ = 10.5) | 3.90 (dd, J$_{4Hb,5H}$ = 10.5) | 3.46 (dd, J$_{4Hb,5H}$ = 10.5) |
| | H$_6$ | 3.84 (d,J$_{5H,6H}$ = 6) | 4.00 (d,J$_{5H,6H}$ = 6) | 3.88 (dd,J$_{5H,6H}$ = 6) |
| | H$_5$ | 4.60 (m) | 4.52 (m) | 4.37 (m) |
| | S—CH = | 6.41 (d,J = 14) | 6.42 (d,J = 14) | 6.24** (d,J = 14) |
| | N—CH = | 7.59 (d) | 7.60 (d) | 7.18** (d) |
| | =CH—NH | | | 10.65** (d,J = 11) |
| | H$_8$ | | | 4.97 (m,J$_{6H,8H}$ = 9) |

*D$_2$O/CH$_3$CN,
**DMSO—d$_6$/CH$_3$CN
[1]A. G. Brown, D. F. Corbett, A. J, Eglington, and T. T. Howarth, J. Chem. Soc., Chem. Comm., 1977, 523-525.

The biological properties of C-19393S$_2$ are described below. The antibiotic spectrum of C-19393S$_2$ sodium salt against various microorganisms are shown below in Table 4. As is apparent from the table, Antibiotic C-19393S$_2$ is active against gram-positive and gram-negative bacteria.

TABLE 4

Antimicrobial Spectrum of Antibiotic C-19393S$_2$ Disodium Salt

| Test Organism | Minimum Inhibitory Concentration (μg/ml) |
|---|---|
| Escherichia coli NIHJ | 12.5–25 |
| Salmonella typhimurium IFO 12529 | 12.5 |
| Klebsiella pneumoniae IFO 3318 | 12.5 |
| Proteus vulgaris IFO 3045 | 100 |
| Proteus mirabilis IFO 3845 | 50 |
| Serratia marcescens IFO 12648 | 25 |
| Alcaligenes faecalis IFO 13111 | 50 |
| Pseudomonas aeruginosa IFO 3080 | >100 |
| Comamonas terrigena IFO 13299 | 6.25 |
| Staphylococcus aureus 209P | 12.5 |
| Sarcina lutea IFO 3232 | 12.5 |
| Bacillus subtilis IFO 3513 | 12.5 |
| Bacillus cereus IFO 3460 | >100 |

Note
Medium: Bouillon agar

Antibiotic C-19393S$_2$ also possesses a strong betalactamase inhibiting activity and, therefore, it increases markedly the sensitivity of various bacteria which exhibit resistance to penicillin derivatives and/or cephalosporin derivatives, to such derivatives. The increasing effect on the antimicrobial activity of ampicillin and cefotiam by C-19393S$_2$ is shown in Table 5.

TABLE 5

Increasing Effect on Antimicrobial Activity of Ampicillin and Cefotiam by C-19393S$_2$

| Test Organism | C-19393S$_2$ | Minimum Inhibitory Concentration ($\mu$g/ml) Ampicillin | Cefotiam |
|---|---|---|---|
| *Escherichia coli* TN 659 | 0 | >800 | 0.2 |
|  | 1 $\mu$g/ml | 3.13 | 0.1 |
|  | 5 $\mu$g/ml | ≦0.003 | 0.006 |
| *Klebsiella pneumoniae* TN 1725 | 0 | 800 | 200 |
|  | 1 $\mu$g/ml | 50 | 0.2 |
|  | 5 $\mu$g/ml | 0.78 | 0.02 |
| *Proteus vulgaris* TN 224 | 0 | 400 | 200 |
|  | 1 $\mu$g/ml | 1.56 | 0.2 |
|  | 5 $\mu$g/ml | 1.56 | 0.2 |

*Clinically isolated strains having the ability to produce beta-lactamase
Medium: Heart Infusion Agar (Eiken Chemical Co., Japan)

As is apparent from the above antimicrobial spectrum, C-19393S$_2$ obtained in accordance with the present invention exhibits an antimicrobial activity against gram-positive and gram-negative bacteria. Accordingly, C-19393S$_2$ can be used for treating bacterial infections in mammals (for example, mouse, rat, dog, human being) and avian species (for example, domestic fowl, duck).

To use C-19393S$_2$ as an agent for treating, for example, *E.coli* infections, C-19393S$_2$ is dissolved in physiological saline solution to prepare an injectable solution which can be administered parenterally, e.g., subcutaneously or intramuscularly at a dose of 2 to 200 mg/kg/day, preferably 5 to 50 mg/kg/day. Also, for oral administration, Antibiotic C-19393S$_2$ is blended with lactose and encapsulated to prepare a capsule preparation which can be administered at a dose of 10 to 500 mg/kg/day, preferably 20 to 200 mg/kg/day.

Further, C-19393S$_2$ obtained in accordance with the present invention can be used as a disinfectant. For example, a liquid preparation which can be prepared by dissolving C-19393S$_2$ in distilled water at a concentration of 0.1 to 1.0 w/v % or an ointment containing 2 to 50 mg, preferably 5 to 20 mg, of C-19393S$_2$ per 1 g of white petrolatum or lanolin as a base can be used as a bactericide or disinfectant for hands, legs, eyes, ears, etc. of the above animals.

As is apparent from the results shown in Table 4, Antibiotic C-19393S$_2$ exhibits a beta-lactamase inhibiting activity and, therefore, markedly increases the sensitivity of penicillin-or cephalosporin-resistant bacteria to ampicillin or cefotiam due to its ability to produce beta-lactamase. Accordingly, C-19393S$_2$ can be used for treatment of infections in mammals (for example, mouse, rat, dog, human being) and avian species (for example, domestic fowl, duck), in particular, bacterial infections due to beta-lactam antibiotic-resistant bacteria, in combination with penicillin or cephalosporin antibiotics.

When C-19393S$_2$ is used in combination with other beta-lactam type agents for the treatment of infections by, for example, beta-lactam antibiotic-resistant *E. coli*, equal amounts of C-19393S$_2$ and ampicillin are dissolved in physiological saline to prepare an injectable solution which can be administered parenterally, e.g., subcutaneously or intramuscularly, at a dose of 0.1 to 20 mg/kg/day, preferably 0.5 to 5 mg/kg/day. C-19393S$_2$ can also be administered orally at a dose of 1 to 200 mg/kg/day, preferably 5 to 100 mg/kg/day as capsules each containing an equal proportion of C-19393S$_2$ and cephalexin.

When C-19393S$_2$ is used as disinfectant, a liquid preparation, for example, an aqueous solution containing C-19393S$_2$ at a concentration of 0.1 to 10 w/v% and benzylpenicillin at a concentration of 0.1 to 1.0 w/v%, or an ointment containing 5 to 20 mg of C-19393S$_2$ and 5 to 20 mg of benzylpenicillin per 1 g of white petrolatum or lanolin as a base can be used as a bactericide or disinfectant for hands, legs, eyes, ears, etc. of the above animals.

Antibiotic C-19393S$_2$ is also expected to be very useful as an intermediate for the synthesis of novel types of pharmaceuticals. The antibiotic of the present invention is stable in aqueous solution in a neutral pH region.

The physiological properties of C-19393H$_2$ are described below.

The antimicrobial spectrum of the sodium salt of C-19393H$_2$ against various microorganisms is shown in Table 6 and, as is apparent from the results shown in Table 6, Antibiotic C-19393H$_2$ exhibits antibacterial activity against gram-positive and gram-negative bacteria.

TABLE 6

Antimicrobial Spectrum of Sodium Salt of Antibiotic C-19393H$_2$

| Test Organism | Minimum Inhibitory Concentration ($\mu$g/ml) |
|---|---|
| *Escherichia coli* NIHJ | 0.08 |
| *Salmonella typhimurium* IFO 12529 | 0.31 |
| *Klebsiella pneumoniae* IFO 3318 | 0.31 |
| *Proteus vulgaris* IFO 3045 | 5 |
| *Proteus mirabilis* IFO 3845 | 5 |
| *Serratia marcescens* IFO 12648 | 0.31 |
| *Alcaligenes faecalis* IFO 13111 | 5 |
| *Pseudomonas aeruginosa* IFO 3080 | 10 |
| *Comamonas terrigena* IFO 13299 | 0.16 |
| *Staphylococcus aureus* 209P | 0.63 |
| *Sarcina lutea* IFO 3232 | 0.31 |
| *Bacillus subtilis* IFO 3513 | 0.31 |
| *Bacillus cereus* IFO 3460 | 10 |

Note
Medium: Bouillon agar

As shown in Table 6 above, Antibiotic C-19393H$_2$ obtained in accordance with the present invention has antimicrobial activity against gram-positive and gram-negative bacteria and, thus, can be used for the treatment of bacterial infections in mammals, for example, mouse, rat, dog, human being and the like and in avian species, for example, domestic fowl, duck and the like.

To use C-19393H$_2$ as an agent for treating, for example, an *E. coli* infection, C-19393H$_2$ is dissolved in physiological saline solution to prepare an injectable solution which can be administered parenterally, e.g., subcutaneously or intramuscularly at a dose of 0.1 to 50 mg/kg/day, preferably 0.5 to 20 mg/kg/day. Also, for oral administration, Antibiotic C-19393H$_2$ is blended with lactose and encapsulated to prepare a capsule preparation which can be administered at a dose of 1 to 100 mg/kg/day, preferably 5 to 50 mg/kg/day.

Further, C-19393H$_2$ obtained in accordance with the present invention can be used as disinfectants. For example, a liquid preparation prepared by dissolving C-19393H$_2$ in distilled water at a concentration of 0.01 to 0.1 w/v% or an ointment containing 0.2 to 20 mg, preferably 1 to 1 mg, of C-19393H$_2$ per 1 g of white petrolatum or lanolin as a base can be used as a bactericide or disinfectant for hands, legs, eyes, ears, etc. of the above animals.

Antibiotic C-19393H$_2$ is also expected to be very useful as an intermediate for the synthesis of novel types of pharmaceuticals. The antibiotic of the present invention is stable in aqueous solution in a neutral pH region.

As described above, MM-4550 can be exemplified as antibiotic relatively similar to the present Antibiotics C-19393S$_2$ and H$_2$. However, MM-4550 is structually different from C-19393S$_2$ and H$_2$, and MC 696-SY2-A [Maeda et al., The Journal of Antibiotics, Vol. 30, pages 770-772, 1977] which is the same substance as MM-4550 is very unstable [Umezawa et al., The Journal of Antibiotics, Vol. 26, pages 51-54, 1973], whereas C-19393S$_2$ and H$_2$ are stable compounds.

The present invention is further illustrated in greater detail by the following Examples which, however, are not to be construed as limiting the present invention. Unless otherwise indicated, all percents are by weight/volume.

EXAMPLE 1

A culture of Streptomyces sp. strain C-19393 (IFO 13886, ATCC 31486) was grown on 200 ml of T Medium charged into a 1 l Erlenmeyer flask to obtain spores. The resulting spores were then suspended in sterile water at a concentration of $1.2 \times 10^8$ living cells/ml. The spore suspension was diluted with sterile water to a volume of 10 times the original volume and 1 ml of the diluted suspension was used to inoculate 40 ml of a seed medium in a 200 ml Erlenmeyer flask. The inoculated seed medium was then cultivated on a rotatory shaker at 28° C. for 2 days. The resulting culture was used to inoculate 500 ml of a seed culture medium charged into a 2 l Sakaguchi shake flask and the inoculated seed medium was cultivated on a reciprocating shaker at 28° C. for 2 days. The seed culture thus obtained was transferred to a 50 l stainless steel fermentation tank containing 30 l of a seed medium containing 15 ml of Actocol (Takeda Chemical Industries, Ltd., Japan) and cultivated at 28° C. for 3 days, with aeration at 30 l/minute and agitation at 280 r.p.m. The culture broth was transferred to a 2 m$^3$ content fermentation tank containing 1.2 m$^3$ of a main culture medium and cultivated at 30° C. for 5 days, with aeration at 840 l/minute and agitation at 180 r.p.m. The seed medium used above was composed of 20 g of glucose, 30 g of soluble starch, 10 g of raw soybean meal, 10 g of corn steep liquor, 5 g of Polypepton (Daigo Nutritive Chemicals, Ltd., Japan), 3 g of sodium chloride and 5 g of precipitated calcium carbonate per 1 l of the medium which had been adjusted to a pH of 7.0 prior to sterilization, and the main culture medium used above was composed of 30 g of glucose, 30 g of soluble starch, 15 g of defatted soybean meal, 15 g of cottonseed flour, 0.25 g of potassium dihydrogen phosphate, 0.6 g of potassium monohydrogen phosphate, 0.002 g of cobalt chloride and 0.5 g of Actocol per 1 l of the medium which had been adjusted to a pH of 7.0 prior to sterilization. All the media used above were steam sterilized at 120° C. for 20 minutes.

The fermentation broth thus obtained was filtered with Hyflo-Supercel (Jhones Manville Co., United States) to obtain 1230 l of a filtrate which was then adjusted to pH 6.3 and passed through a column packed with 100 l of activated carbon. Then, C-19393S$_2$ and H$_2$ were eluted from the column with 300 l of water and 700 l of 7% aqueous isobutanol, respectively. The eluate containing C-19393S$_2$ was passed through a column of Dowex 1×2 (Cl$^-$ form, 2 l), and the column was washed with 6 l of water and eluted with 32 l of 5% aqueous sodium chloride. The eluate was adjusted to pH 5 and passed through a column packed with 4 l of activated carbon. After washing with 12 l of water, the desired antibiotic was eluted with 7 l of 8% aqueous isobutanol and 12 l of isobutanol:N/20 aqueous ammonia (8:92), and the eluate was concentrated to a volume of 150 ml under reduced pressure. 1350 ml of methanol was added to the concentrate and the precipitate thus formed was removed by filtration. The filtrate was concentrated to a volume of 200 ml, and passed through a column packed with 300 ml of DEAE-Sephadex A-25 (Cl$^-$ form). The column was washed successively with 0.1M and 0.2M aqueous sodium chloride solutions (each 900 ml) and, thereafter, the desired antibiotic substance was eluted with 1500 ml of 0.4M aqueous sodium chloride. The eluate was adjusted to pH 5 and passed through a column packed with 500 ml of activated carbon. After washing with 1.5 l of water, the column was eluted with 2.5 l of isobutanol:N/20 aqueous ammonia (8:92), and the eluate was concentrated to dryness and acetone was added to the residue to obtain 2.4 g of a pale yellow powder. After dissolving the resulting powder in a small amount of water, the solution was passed through a column packed with 1.2 l of Amberlite XAD-II (100 to 200 mesh) and eluted fractionally with water. The fractions which showed antibiotic activity were pooled and concentrated, and the concentrate was passed through a column packed with 200 ml of QAE-Sephadex A-25(Cl$^-$ form). After washing with 600 ml of 0.1M aqueous sodium chloride, the column was eluted with 1.2 l of 0.2M aqueous sodium chloride. The eluate was adjusted to pH 5 and passed through a column packed with 600 ml of activated carbon. After washing the column with 1.8 l of water, the column was eluted with 3 l of isobutanol:N/20 aqueous ammonia (8:92). The eluate was concentrated to dryness and acetone was added to the residue to obtain 1.07 g of a powder. A 620 mg portion of the powder thus obtained was dissolved in a small amount of water and the solution was passed through a column packed with 360 ml of Amberlite XAD-II (100 to 200 mesh). The column was then eluted and fractionated with water, and each of the fractions which revealed antibiotic activity was subjected to analysis by liquid chromatography as described above. The fractions which showed a single peak were pooled and concentrated to dryness, and acetone was added to the concentrate to obtain 136 mg of Antibiotic C-19393S$_2$ disodium salt as white powder.

EXAMPLE 2

The eluate of C-19393H$_2$ obtained in Example 1 was passed through a column of Dowex 1×2 (Cl$^-$ form, 12 l), and the column was washed with 6 l of water and eluted with 180 l of 5% aqueous sodium chloride. The eluate was passed through a column packed with 25 l of activated carbon. After washing with 75 l of water, the desired antibiotic was eluted with 175 l of isobutanol:water (7:93), and the eluate was concentrated to a volume of 2 to 3 l under reduced pressure. 15 l of methanol was added to the concentrate and the precipitate thus formed was removed by filtration. The filtrate was concentrated to a volume of 2 l, and passed through a column packed with 5 l of Diaion HP-20(50 mesh). The column was then eluated and fractionated with 5 l of water and 10 l of methanol:water (1:9). The active fractions were pooled and concentrated, and the concentrate was passed through a column packed with 3 l of DEAE-Sephadex A-25 (Cl⁻ form). The column was washed with 9 l of 0.02M aqueous sodium chloride and the desired antibiotic was eluted and fractionated with 12 l of 0.05M aqueous sodium chloride. The active fractions were passed through a column packed with 2 l of Diaion HP-20 (50 mesh) which had been treated with 4 l of aqueous sodium chloride and, after washing with 10 l of 5% aqueous sodium chloride, the active principle was eluted and fractionated with 10 l of methanol:5% aqueous sodium chloride (5:95) and 10 l of methanol:5% aqueous sodium chloride (1:9). The active fractions were passed through a column packed with 500 ml of activated carbon and, after washing with 1.5 l of water, eluted with 2.5 l of 7% aqueous isobutanol. The eluate was concentrated, and the concentrate was passed through a column packed with 1 l of Diaion HP-20 (50 to 100 mesh) and eluted and fractionated with water. The fractions having antibiotic activity were pooled and concentrated, and the concentrate was passed through a column packed with 200 ml of QAE-Sephadex A-25 (Cl⁻ form) which had been treated with 400 ml of 0.02M aqueous sodium chloride. The column was then successively eluted with 0.02M, 0.03M and 0.04M aqueous sodium chloride solutions (each 1 liter). The active fractions were passed through a column packed with 200 ml of activated carbon and, after washing with 0.6 l of water, eluted with 1 l of 7% aqueous isobutanol. The eluate was concentrated, and propanol was added to the concentrate to prepare 90% aqueous propanol which was then subjected to an Avicel column chromatography which had been treated with 90% aqueous propanol. The column was eluted with 90% aqueous propanol. The active fractions were concentrated and the concentrate was subjected to column chromatography on 350 ml of Amberlite XAD-II (100 to 200 mesh) and the column was eluted with water. The active fractions were concentrated and the concentrate was subjected to a preparative high performance liquid chromatography using RP-18(E. Merck & Co., West Germany) as a carrier and eluted with 10% methanol in 0.02M phosphate buffer (pH 6.3). The active fractions were passed through a column packed with 40 ml of Diaion HP-20 (100 to 200 mesh) and fractionally eluted with water. Each of the fractions which revealed antimicrobial activity was subjected to the analysis of liquid chromatography as described above. The fractions which showed a single peak were pooled and freeze-dried to obtain 12 mg of C-19393H$_2$ as white powder.

EXAMPLE 3

1150 l of a culture broth filtrate prepared by a procedure similar to that described in Example 1 was adjusted to pH 5 and passed through a column packed with 100 l of activated carbon. After washing with 300 l of water, the column was eluted with 350 l of isobutanol:0.02N sodium hydroxide (8:92). The eluate was passed through a column packed with 10 l of Diaion SA-21A (Cl⁻ form) and, after washing with 30 l of water, the column was eluted with 100 l of 5% aqueous sodium chloride. The eluate was then passed through a column packed with 20 l of Diaion HP-20 (50 mesh) which had been treated with 40 l of 5% aqueous sodium chloride and the column was washed with 20 l of 5% aqueous sodium chloride. Then, C-19393S$_2$ and H$_2$ were eluted from the column with 40 l of water and 60 l of methanol:5% aqueous sodium chloride (5:95), respectively. The eluate containing C-19393S$_2$ was adjusted to pH 5 and passed through a column packed with 2 l of activated carbon. After washing with 6 l of water, the column was eluted with 10 l of 8% isobutanol-N/20 aqueous ammonia and the eluate was concentrated. The concentrate was passed through a column packed with 200 ml of QAE-Sephadex A-25 (Cl⁻ form) and, after washing with 1 l of 0.2M aqueous sodium chloride, the column was eluted with 1 l of 0.4M aqueous sodium chloride. After the eluate was de-salted by activated carbon chromatography, it was subjected to column chromatography with Amberlite XAD-II and worked up in a similar manner to that of Example 1 to obtain 100 mg of Antibiotic C-19393S$_2$ disodium salt as white powder.

EXAMPLE 4

The eluate of C-19393H$_2$, obtained in Example 3, was adjusted to pH 5 and passed through a column packed with 2 l of activated carbon. After washing with 6 l of water, the column was eluted with 10 l of isobutanol:N/20 aqueous ammonia (8:92) and the eluate was concentrated. The concentrate was passed through a column packed with 200 ml of QAE-Sephadex A-25 (Cl⁻ form) and, after washing with 1 l of 0.02M aqueous sodium chloride, the column was eluted with 1 l of 0.04M aqueous sodium chloride. After the eluate was de-salted by activated carbon chromatography, it was subjected to column chromatography on 200 ml of Diaion HP-20 (100 to 200 mesh) and the column was eluted and fractionated with water. The fractions which showed a single peak on liquid chromatography were pooled and concentrated, and the concentrate was freeze-dried to obtain 48 mg of C-19393H$_2$ sodium salt as white powder.

What we claim is:

1. An antibiotic substance represented by the formula wherein R represents —SO$_3$H or a pharmaceutically acceptable salt thereof.

* * * * *